(12) United States Patent
Zirkle, Jr.

(10) Patent No.: US 7,066,943 B2
(45) Date of Patent: Jun. 27, 2006

(54) METHOD AND APPARATUS FOR LOCATING AND STABILIZING AN ORTHOPEDIC IMPLANT

(76) Inventor: Lewis G. Zirkle, Jr., 875 Swift Ave., Richland, WA (US) 99352

( * ) Notice: Subject to any disclaimer, the term of this patent is extended or adjusted under 35 U.S.C. 154(b) by 285 days.

(21) Appl. No.: 10/694,615

(22) Filed: Oct. 23, 2003

(65) Prior Publication Data

US 2004/0082955 A1     Apr. 29, 2004

Related U.S. Application Data

(63) Continuation-in-part of application No. 10/109,956, filed on Mar. 29, 2002, now abandoned.

(60) Provisional application No. 60/280,734, filed on Mar. 30, 2001.

(51) Int. Cl.
*A61B 17/58*     (2006.01)
(52) U.S. Cl. ........................................... 606/98
(58) Field of Classification Search ............... 606/62, 606/63, 96, 98
See application file for complete search history.

(56) References Cited

U.S. PATENT DOCUMENTS

| | | | | |
|---|---|---|---|---|
| 4,846,162 A | * | 7/1989 | Moehring | 606/67 |
| 5,057,103 A | * | 10/1991 | Davis | 606/63 |
| 5,395,317 A | * | 3/1995 | Kambin | 604/506 |
| 6,185,595 B1 | * | 2/2001 | Hori et al. | 708/402 |
| 6,197,029 B1 | * | 3/2001 | Fujimori et al. | 606/62 |

* cited by examiner

*Primary Examiner*—Cary E. O'Connor

(57) ABSTRACT

The invention is a device, and a method of using the device, for securing an intermedullary (IM) orthopedic nail within a fractured long bone of a human or large animal. The nail is provided with a plurality of target apertures, a portion of which are located above and below the fracture point of the bone. The device further comprises a jig adapted to be securely affixed to the IM nail, the jig having proximal and distal target arms, each having a plurality of apertures adapted to align with the target apertures. When properly secured, the apertures of the jig align with the target apertures of the nail, and alignment devices are provided to accurately drill variable diameter holes through the bone cortex at the target apertures. A leading end of the slot finder is provided with a cross-sectional geometry substantially identical to the cross-sectional geometry of the target apertures, and enables the surgeon to be sure the slot finder is in the target aperture of the nail. The surgeon is assured that he has accurately located the target aperture because the rotational movement of the slot finder is limited to a maximum of about 20 degrees because of the securement of the leading end within the target aperture. The slot finder is further provided with a bearing surface that prevents further insertion of the slot finder within the target aperture, further providing the surgeon with assurance of the proper location of the slot finder. A unique screw secures the nail in place; the screw is provided with a larger, diameter threaded portion and a smaller diameter threaded portion. A further aspect of the invention is an apparatus for forcibly removing the nail from the bone.

13 Claims, 15 Drawing Sheets

METHOD AND APPARATUS FOR LOCATING AND STABILIZING AN ORTHOPEDIC IMPLANT

CLAIM OF PRIORITY

This application claims priority under 35 U.S.C. 120 of prior provisional patent application Ser. No. 60/280,734 filed Mar. 30, 2001 now abandoned and is a continuation in part of non-provisional patent application Ser. No. 10/109,956 filed Mar. 29, 2002 now abandoned.

FIELD OF THE INVENTION

The present invention relates to orthopedic implant devices, and more specifically, an orthopedic implant device that requires little or no sophisticated electronic apparatus' in order to locate and stabilize an intermedullary (IM) nail inserted longitudinally within a fractured long bone in an animal extremity. In particular, the invention permits the precise location of proximal and distal fixation slots in IM nails and accurate placement of locking bone screws without need for real time x-ray imaging. The present invention avoids the problems incident in state-of-the-art processes wherein devices must be provided to align axial holes in the bone with blind holes in the implant.

BACKGROUND OF THE INVENTION

In many surgical environments, the use of sophisticated medical procedures is either not possible, or not cost effective. For example when medical doctors in developed countries set IM nails and interlocking screws in fractured bones, the procedure is accomplished using real-time imaging (x-ray or otherwise). However, when performing this, operation in undeveloped countries, or when veterinarians set fractures in animals even in developed countries one may not have access to equipment and procedures available to the medical community in more developed countries. The present invention relates to an apparatus, and a method of using the apparatus, useful in the orthopedic repair of fractures of long bones (generally, but not exclusively, the tibia and femur) of animals. The fracture of the femur or tibia in humans resident in undeveloped countries, or the fracture of the foreleg in horses, may necessitate the use of technology that is relatively unsophisticated when compared to that used in hospitals in, for example, the United States.

The present invention comprises an apparatus that is simple to use and may be utilized by medical personnel in undeveloped countries without ready access to costly equipment that requires well-trained operators, or by surgeons concerned with the amount of radiation received by the patient and surgeon using real-time imaging. Alternatively, it may be used in more highly developed countries if the procedure does not require more highly developed technology, or in situations where (for example, on battlefields) emergency operations must be performed as quickly as possible. Additionally, there may be application of this technology by veterinarians to livestock where more costly procedures are not warranted.

The art of repair of fractured long bones has developed over decades, and for repair of serious fractures of long bones the use of IM nails and transverse screws is now well known. The screws secure the nail (when within the medullary canal) against relative axial, longitudinal and rotational movement, thereby enabling fixation of the fracture against axial, longitudinal and rotational displacement. The nails are inserted longitudinally through the medullary canal of the bone, and transverse bores must be made in the bone into which are inserted screws or pins.

The history of devices attempting to offer a dependable repeatable method for locating IM nails and securing them within the medullary canal without the aid of x-ray imaging has been largely unsuccessful. The primary problem has been the orientation of the IM nail, and the securing slots therein, as they are affected by the internal shape of each patient's individual medullary canal. The present invention provides an accurate and reproducible apparatus and method for locating the IM nail apertures even when the nail has been deflected within the bone.

Prior art devices have attempted the correct positioning of the transverse bores by, for example, the device disclosed in U.S. Pat. No. 4,976,258. A fitting is adapted to hold a telescopic guide member which engages the window of an image converter or the front portion of the housing of an X-ray source such that the axis of the guide member is coaxial with the X-ray beam axis, thereby assuring proper alignment of the axial bores with apertures in the nail.

U.S. Pat. No. 4,848,327, Perdue, discloses a method of emplacing an orthopedic nail into the IM area of a long bone, using a fluoroscope assembly to develop an image on a monitor. This image enables a physician to adjust the fluoroscope assembly until the X-rays from the fluoroscope are coaxially aligned with nail screw holes in the nail, thereby ensuring that the screws are properly aligned.

Another method of attempting to accomplish the same result is illustrated in U.S. Pat. No. 5,478,343, Ritter. This patent discloses a targeting device for making holes in cortical bone for bone nails. An X-ray machine is used to maintain the drill in position during drilling, with an aligned telescopic guide then used to complete the drilling operation.

U.S. Pat. No. 5,584,838, Rona, et al. discloses a method of aligning a drill for drilling transverse holes in bones. A magnetic field with maximum strength along an axis of a transverse hole decreases in strength in directions radially away from the axis. Sensors are provided at axially spaced locations on a drill guide detect deviation of the drill guide. An X-ray machine emits radiation along a longitudinal axis and an X-ray collector is used in conjunction with a visible laser light in U.S. Pat. No. 5,031,203, Trecha. A target grid member is disposed on the X-ray collector portion for targeting the visible laser light in coaxial relationship with the axis of the X-ray radiation gun. U.S. Pat. No. 4,969,889 Greig discloses an instrument for locating apertures in an IM nail. A guide sleeve is substantially translucent when subjected to X-ray visualization, and a pin is opaque so that the pin can be aligned with the hole of the IM nail.

The invention of U.S. Pat. No. 4,667,664, Taylor et al. comprises a method of installing an implanted orthopedic IM nail in the medulla of a fractured long bone. The inventive device is intended to locate the blind screw holes in the end of the nail, so that screws can be quickly and accurately be emplaced to secure the nail within the bone. A target mechanism is aligned using a standard X-ray device, and is arranged so that it can be moved in four degrees of movement, thereby facilitating precise coaxial alignment with blind screw holes in the nail. Finally, U.S. Pat. No. 6,093,192 discloses a device for proximal and distal locking of IM nails without X-rays.

SUMMARY OF THE INVENTION

The present invention relates to methods and apparatus for locating and stabilizing an orthopedic IM nail inserted longitudinally within a fractured long bone without the need for expensive and sophisticated apparatus' to locate apertures in the nail. Generally speaking, orthopedic IM nails are provided with one or two apertures in each end, such that screws may be secured transversely through the bone cortex and through the holes to maintain the nail (and therefore the bone) in a fixed and secure alignment so as to ensure rapid and accurate healing of the bone fracture. In use, an orthopedic IM nail is inserted longitudinally into the fractured bone and one or more incisions are made adjacent to the upper and lower end of the nail through the patient's skin and musculature. A drill is inserted through the incision and a radial aperture is drilled through the bone cortex to provide access to the, apertures in the orthopedic nail. In a first embodiment of the invention, a jig is attached to the nail to permit doctors to accurately drill through the nail apertures, thereafter inserting screws through the bone cortex and the nail apertures. In the event the jig does not accurately align the apertures of the nail with the apertures drilled through the bone, a slot finder is provided to make the alignment.

The apparatus of the present invention may find particular application in those cases where sophisticated equipment is not available to locate holes in the "lower" end of the orthopedic nail. Such applications exist, for example, in underdeveloped nations having relatively unsophisticated medical facilities, or in veterinarian applications where the economics of the practice do not permit such instruments.

Therefore, it is an object of the present invention to provide a safe, easily taught and inexpensive apparatus for the fixation of fractures of long bones in both humans and animals.

BRIEF DESCRIPTION OF THE DRAWINGS

FIG. 7A is an enlargement of the leading tip of the slot finder

FIG. 7B is an enlargement of the engagement of the leading tip of the slot finder into a target aperture;

DETAILED DESCRIPTION OF THE INVENTION

Figure 13:
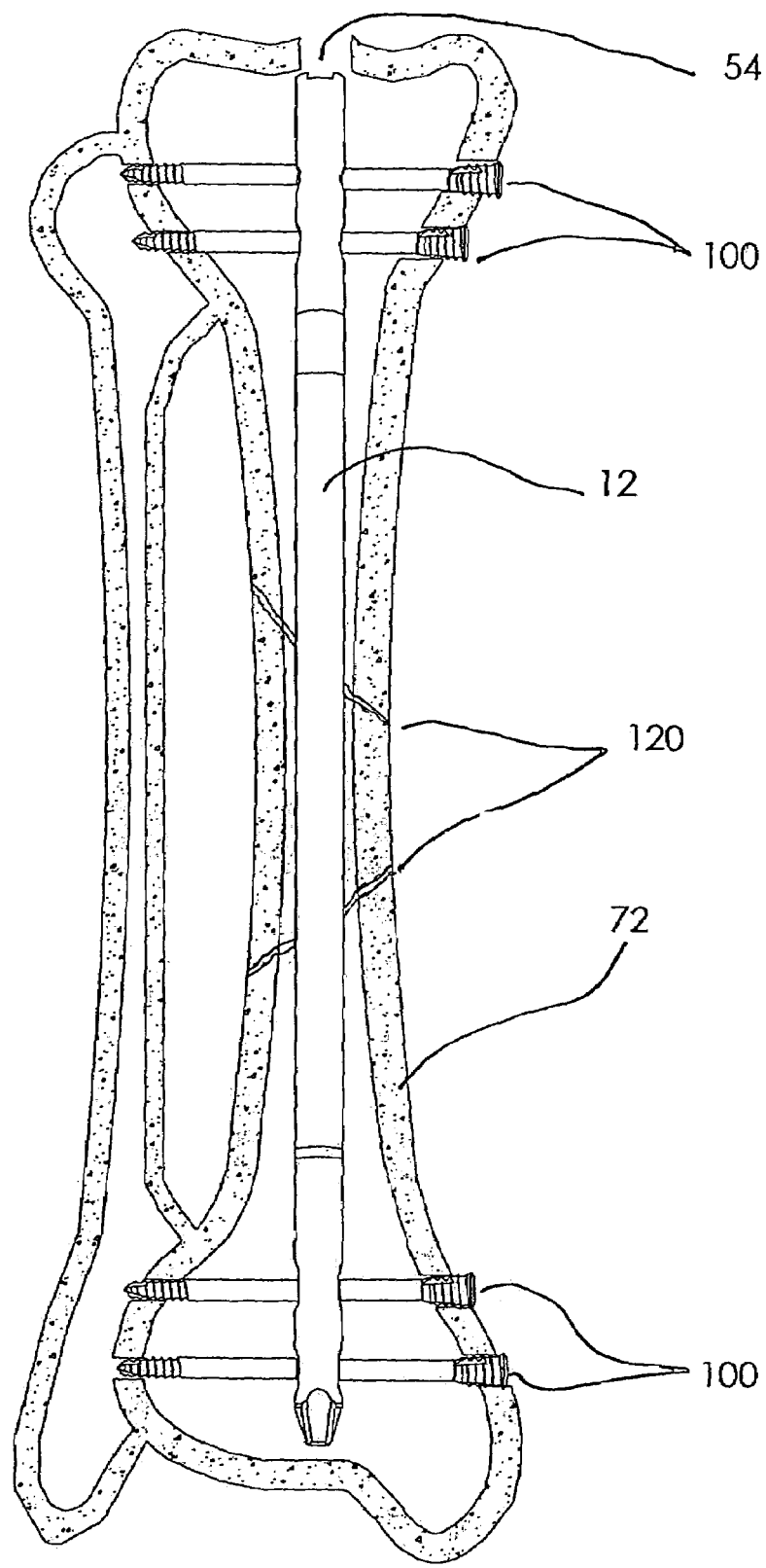
FIG. 13 illustrates an IM nail fully secured within the medullary canal of the bone.

In its broadest embodiment, the apparatus and method of the present invention provide a method of stabilizing a fractured long bone by insertion of an orthopedic intermedullary (IM) nail through them medullary region of the bone, and then using the nail to secure the pieces of the bone in their proper alignment without the need for sophisticated equipment such as fluoroscopes, X-rays, lasers, and the like. When a long bone of the human body, such as the tibia, humerus or femur is fractured, standard procedure is to insert an elongate orthopedic IM nail into the medullary region of the bone, such that the nail extends in both directions beyond the locus of the fracture (indicated at 120 in FIG. 13). Such nails are generally provided with a pair of apertures at each end, so that screws may be inserted through the bone cortex and the nail apertures, thereby securing the nail in place within the bone.

Figure 1:
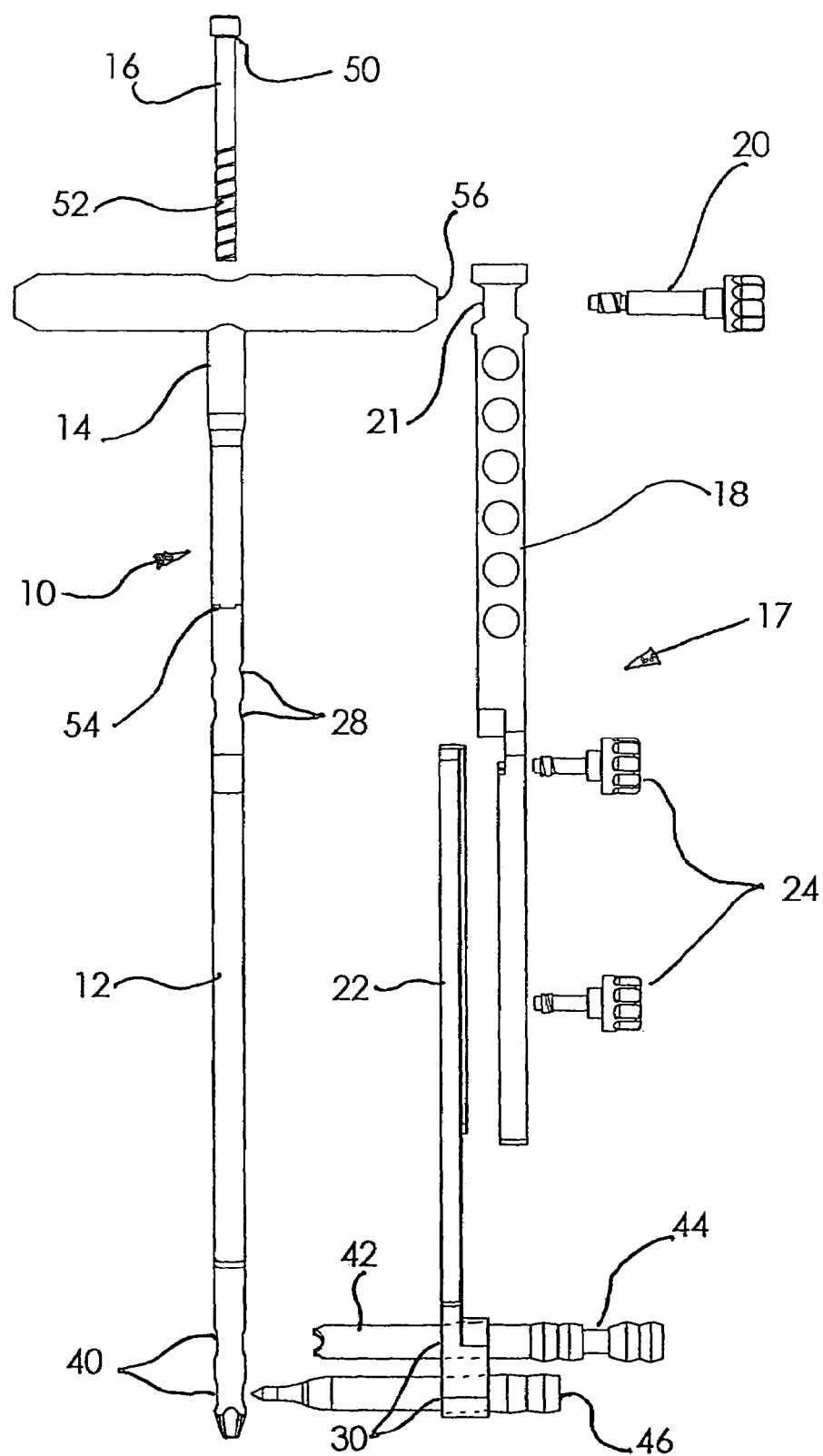
FIG. 1 illustrates the apparatus of the present invention.

As illustrated in FIG. 1, the device 10 of the present invention generally comprises an elongate orthopedic IM nail 12 and a T-handle 14 removably secured thereto. A locking bolt 16 secures the nail 12 to the T-handle 14. A jig 17 comprises a proximal target arm 18 removably affixed to the T-handle 14 with a shoulder cap screw 20 through aperture 21 in proximal target arm 18 and into an aperture 56 in the end of the T-handle 14, while a distal target arm 22 is affixed to the proximal target arm 18 by one or more cap screws 24. The proximal target arm 18 is provided with one or more proximal apertures 26 aligned with proximal apertures 28 in IM nail 12. The distal target arm 22 is likewise provided with one or more distal apertures 30 aligned with distal apertures 40 in the IM nail. As will be described in greater detail below, a cannula 42, drill guide 44 and alignment pin 46 may be provided on the distal target arm 22. The apertures 28 and 40 may have a circular cross-sectional geometry, or they may have a non-circular cross-sectional geometry. It is understood that the apertures 28 and 40 are disposed along a longitudinal axis of the IM nail such that a portion of the apertures are located above the point of fracture, and a portion of the apertures are located below the point of fracture.

Figure 2:
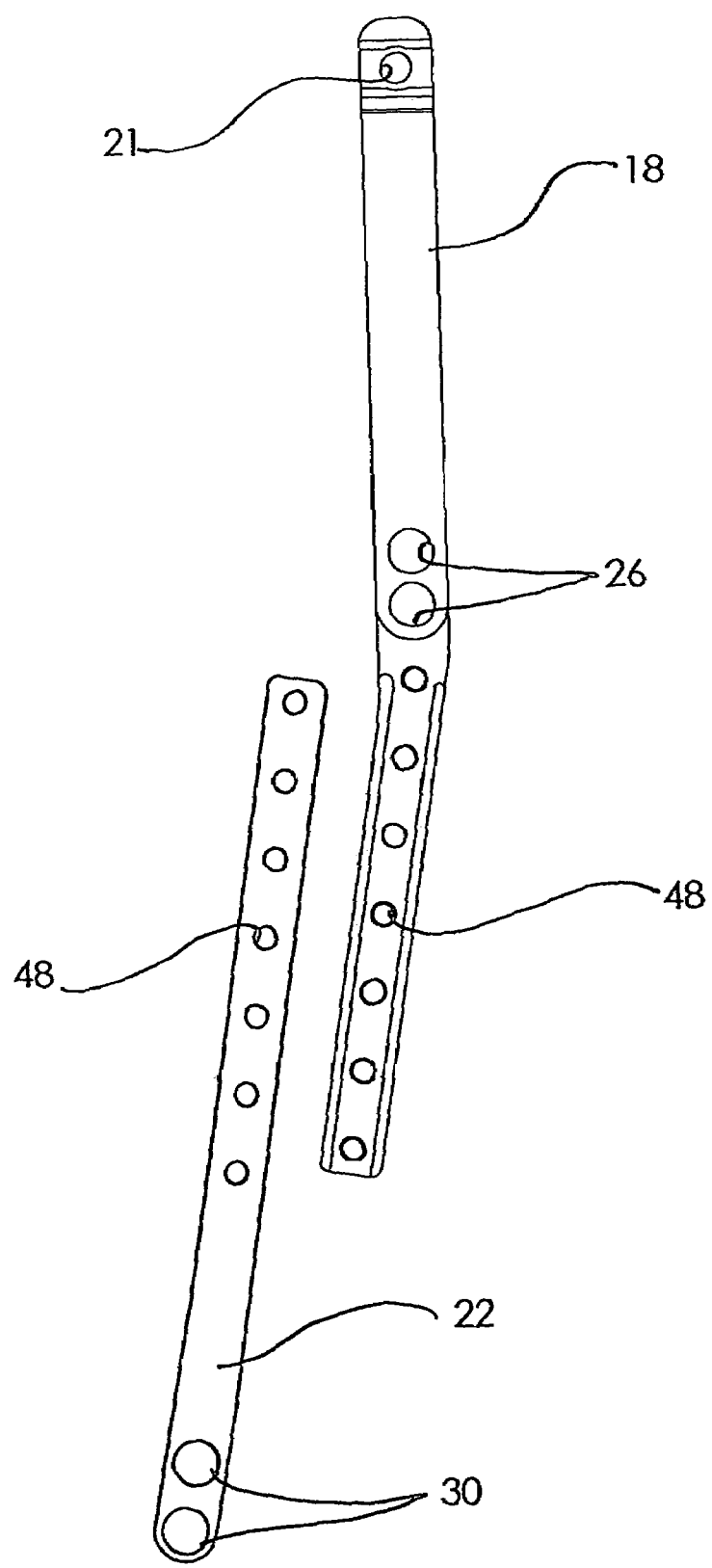
FIG. 2 illustrates the proximal and distal arms of the present invention in side view.

FIG. 2 illustrates the proximal and distal target arms 18, 22 in side view, and illustrates the longitudinal adjustment of the target arms 18, 22 by virtue of a plurality of adjustment apertures 48. The target arms are secured to one another by cap screws 24 once the appropriate apertures 48 are aligned given the length of the IM nail utilized.

Figures 3, 3A:
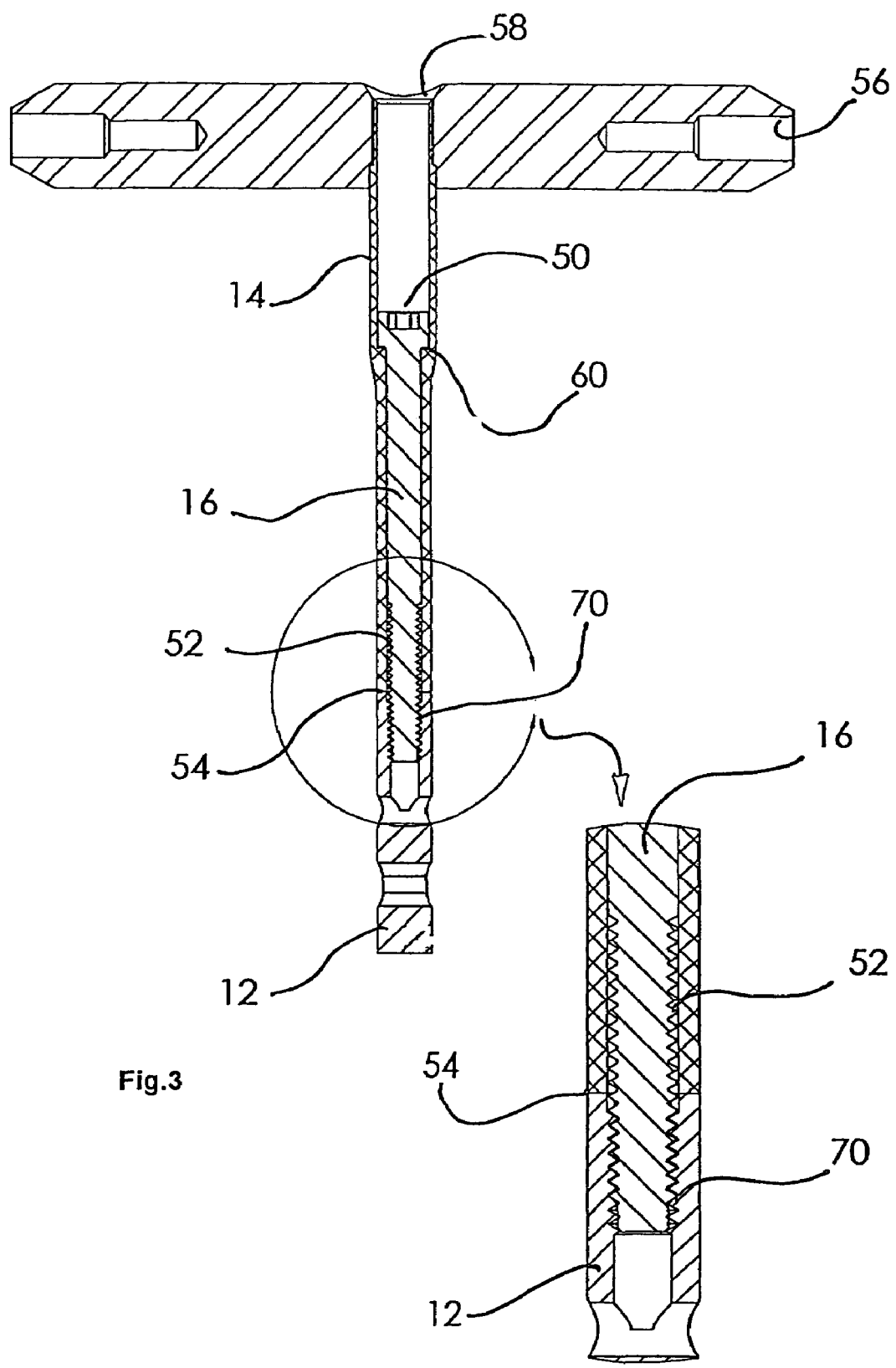
FIG. 3 illustrates the attachment of the T-handle to the IM nail in longitudinal sectional view.
FIG. 3a illustrates in greater detail the point of attachment from FIG. 3.

In order to ensure proper insertion of the IM nail within the medullary canal of the bone, it is required that the T-handle 14 be fixedly secured to the IM nail 12 (FIG. 3). To ensure that the T-handle and the IM nail may be rotated about the longitudinal axis of the IM nail during insertion into the bone, the locking bolt 16 is inserted through aperture 58 in the T-handle and into the proximal end of the IM nail 12. The head 50 of the locking bolt 16 abuts a shoulder 60 within the T-handle, while the treads 52 of locking bolt 16 engage a female threaded portion 70 within the IM nail. The head 50 may be provided with, for example a square or hex slot (not shown) to receive a mating member of a wrench to tighten the bolt 16, thereby locking the T-handle to the IM nail. The T-handle and IM nail may be provided with interlocking tabs 54 to ensure that there is no relative movement there between. The tabs 54 likewise assure that when properly assembled, the apertures 28, 40 of IM nail will properly align with apertures 26, 30 of the jig 17.

Figure 4:
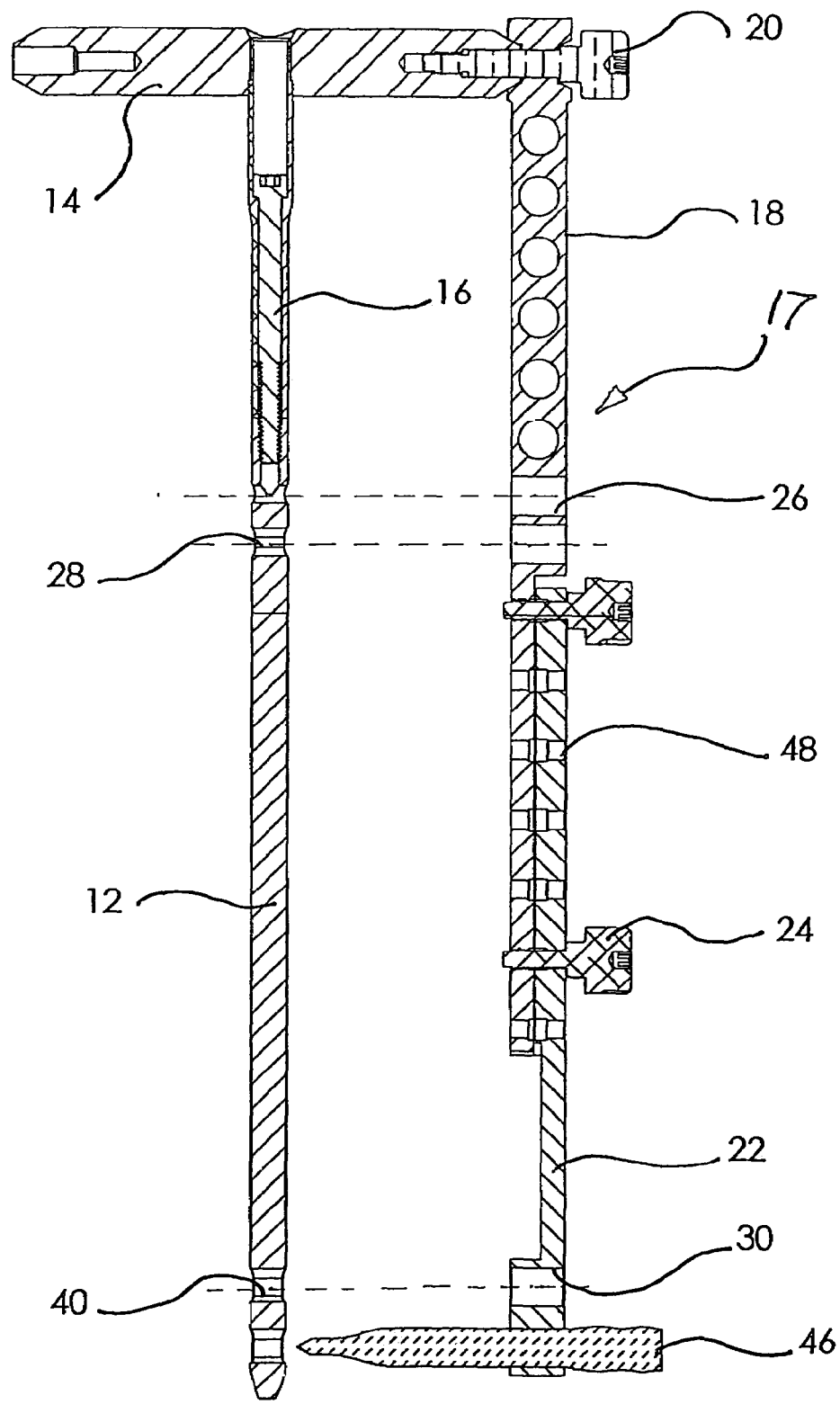
FIG. 4 illustrates the alignment of apertures in the IM nail with apertures in the jig.

FIG. 4 illustrates that location of apertures 28 in the "upper" (proximal) end of IM nail 12 relative to apertures 26 in the proximal arm 18 is relatively easy—the alignment using the present invention is precise and relatively foolproof. However, because the long bones in humans and animals are rarely perfectly straight, and the nail may bend with insertion, orthopedic nails are generally provided with a curvature to match the curvature of the fractured bone. Further, because the orthopedic nails may be as much as 12–24" in length, it is extremely difficult to locate the distal apertures 40 of IM nail 12. Therefore, expensive and sophisticated devices such as those disclosed in U.S. Pat. Nos. 4,848,327, 4,976,258 and 5,478,343 noted above have been developed to ensure proper alignment when distal apertures are drilled through the bone cortex to align with the distal apertures of the IM nail.

Figure 5:
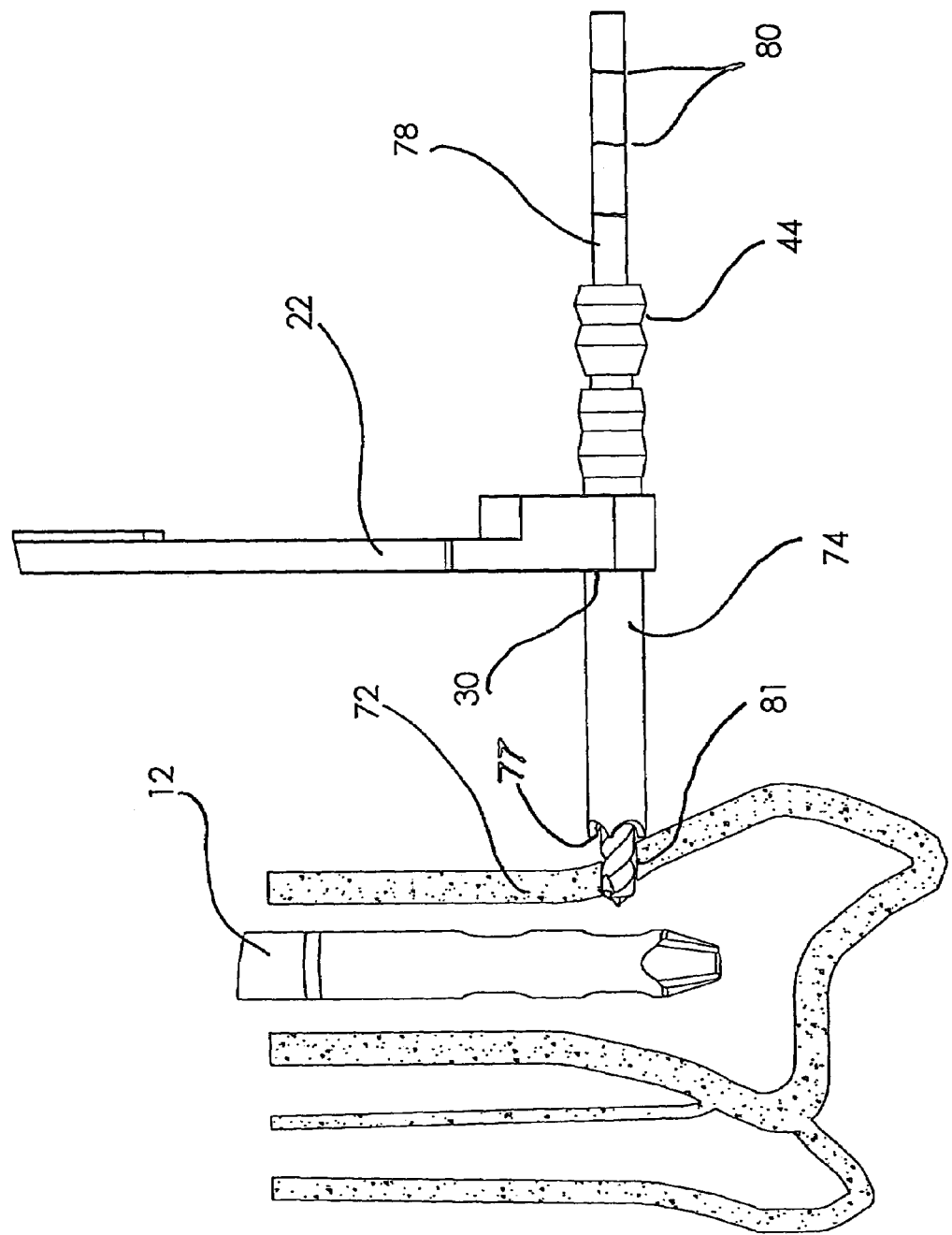
FIG. 5 illustrates the drilling of the large aperture in the near cortex of the bone.
Figure 6:
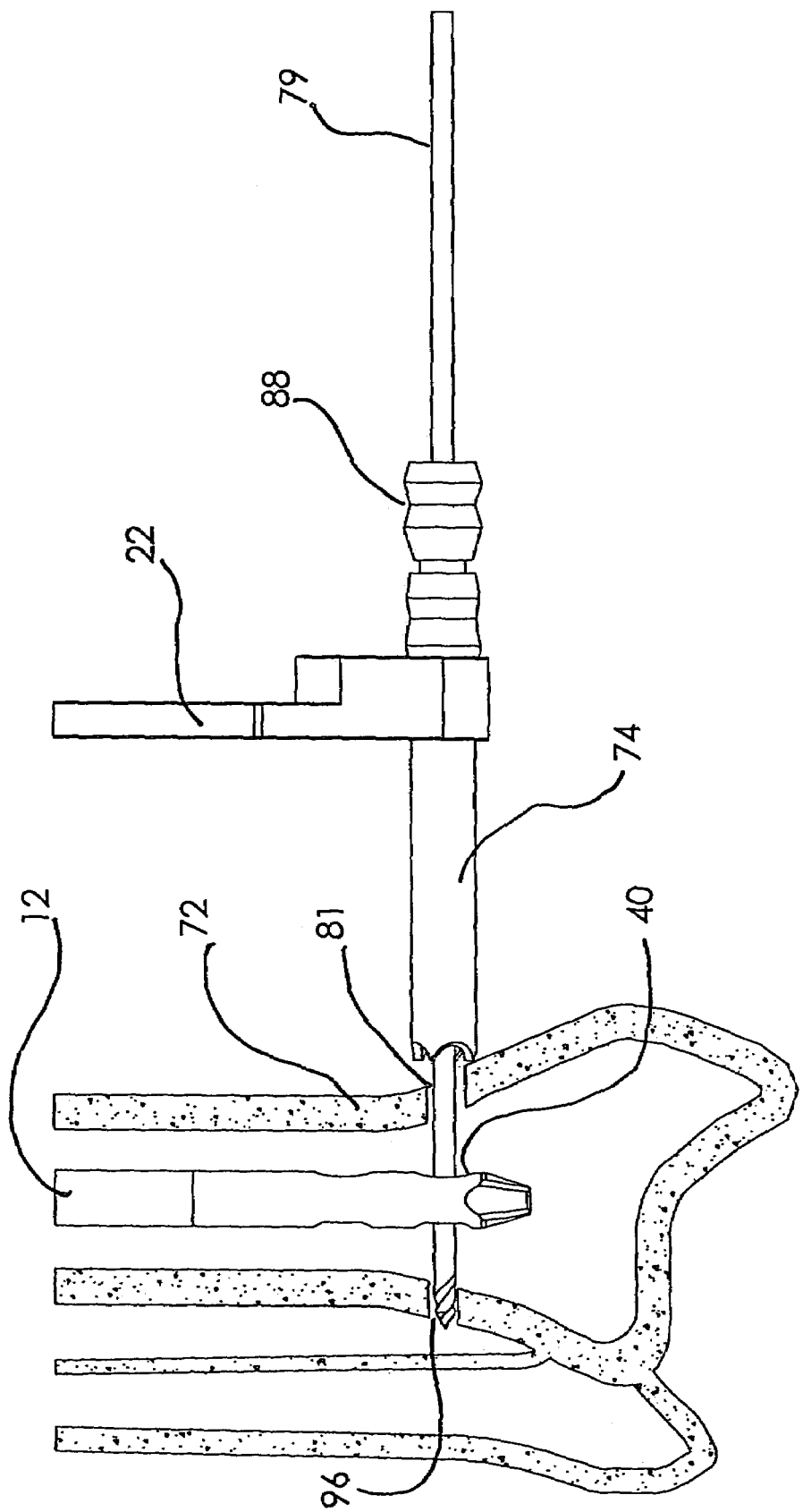
FIG. 6 illustrates the drilling of the small aperture in the far cortex of the bone.

As illustrated herein, the IM, nail is inserted into a human femur. It is to be understood that the environment shown in the drawings and described herein is illustrative only; the apparatus and method disclosed herein can be used in any other elongated bone, either in humans or animals. After the IM nail has been inserted within the bone 72 (FIG. 5), jib 17 is affixed to the T-handle 14 with shoulder cap screw 20. Cannula 74 is inserted through aperture 26 in distal target arm 22 and engages the cortex 76 of bone 72. The leading edge 77 of cannula 74, is preferably provided with means (such as a serrated edge) to engage the bone cortex and prevent rotational movement of the cannula. The first of two drill guides 44 is then inserted into the cannula. A first larger rotary drill bit 78 is inserted through the drill guide 44 and power applied from a drill driver 108 drills a first aperture 81 in the near side bone cortex 72, this first aperture 81 having a first larger diameter. Thereafter, the (first, larger) drill guide 44 is removed and a second, smaller drill guide 88 having a bore slightly larger than that of the corresponding drill bit to be used, is inserted into the cannula (FIG. 6). A smaller diameter drill bit 79 is then inserted into the drill guide through the larger aperture 81 and the target aperture 40 and drills a second smaller aperture 96 into the far side of the bone cortex. The procedure is illustrated herein as being initiated at the distal end of the IM nail but could begin at the proximal end as well. The procedure described herein is essentially identical at both the proximal and distal ends of the IM nail.

Figure 7:
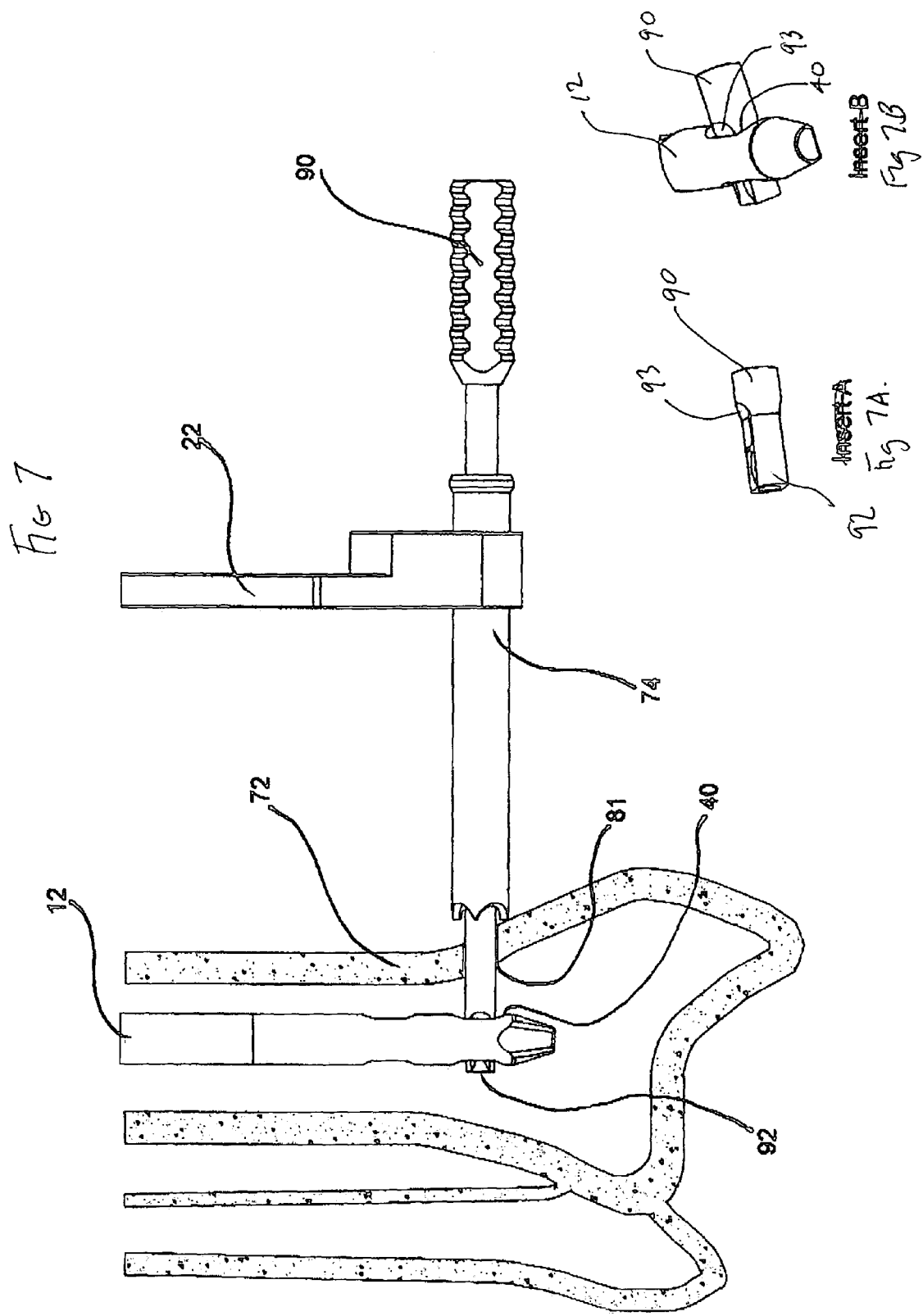
FIG. 7 illustrates the use of the slot finder

In the event that the aperture 40 (or 28) is, not perfectly aligned with the cannula 74, so that the aperture is not immediately located by the smaller drill bit 79, the drill guide 44 may be left in the cannula, and a slot finder 90 (FIG. 7) is inserted through the drill guide 44 (or through the cannula if the drill guide has been removed). The leading end 92 of the slot finder is inserted through the aperture 81 and ascertains whether the near aperture 81 in the bone is aligned with the slot 40 in the nail. The leading end (or tip) 92 of slot finder 90 is preferably engineered with a cross-sectional geometry substantially identical to the cross-sectional geometry of the target apertures, such that the leading end 92 will fit precisely within target apertures 40. The slot finder is also provided with a bearing surface 93 (FIG. 7A) that is adapted to bear against the exterior of the nail (FIG. 7B) so as to prevent further penetration of the slot finder within the nail. Preferably, tip 92 of slot finder 90 is engineered such that when engaged with the slot 40 in the nail, no more than 20 degrees of rotation of the slot finder 90 is possible. If the rotation of the slot finder 90 is thus limited, the surgeon can be confident that the tip of the slot finder is engaged in the apertures (slot) in the nail. Similarly, once the slot finder is engaged with the nail, the bearing 93 prevents further penetration of the slot finder into the target aperture 40 of the nail. The combination of limited rotational movement of the slot finder, with limited lateral movement (penetration) of the slot finder, assures a surgeon that the target aperture 40 has been located.

Much effort, as well as much of the prior art noted above, has been devoted to perfecting a system to enable the surgeon to "find" the target aperture in an orthopedic IM nail. It is believed that the combination of the engineered geometry mating the target aperture geometry with the geometry of the leading tip of applicant's slot finder provides a simple and effective system for locating the target aperture without the need for sophisticated and expensive electronic machinery.

Figure 8:
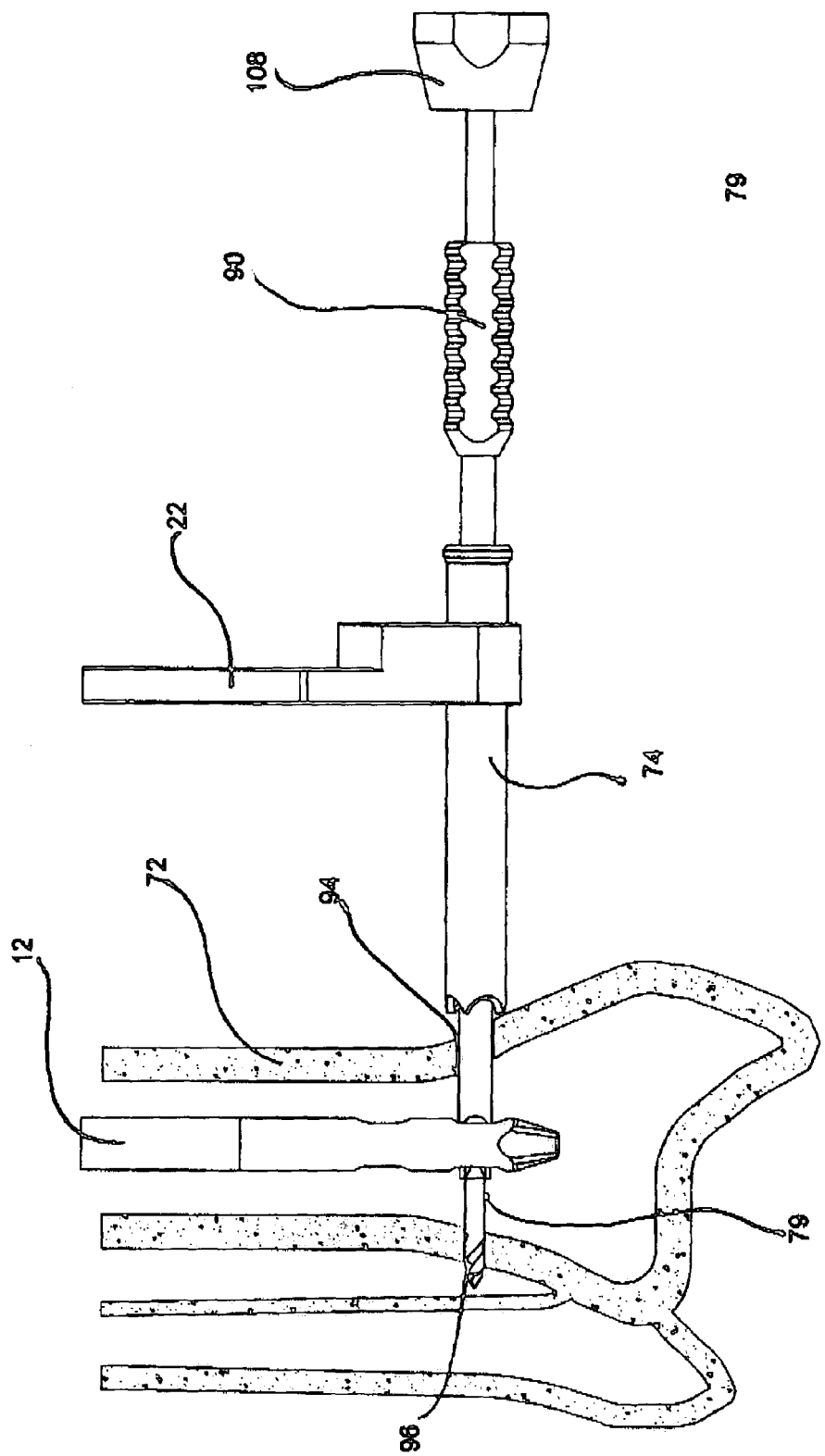
FIG. 8 illustrates the drilling of the far cortex of the bone through the cannulated slot finder.

The slot finder is cannulated so the smaller drill guide can place the second smaller aperture into the far side of bone cortex 96. As illustrated in FIG. 8, the slot finder 90 may be left engaged with the aperture 40, and the smaller drill bit 79 provided co-axially therethrough.

Figure 9:
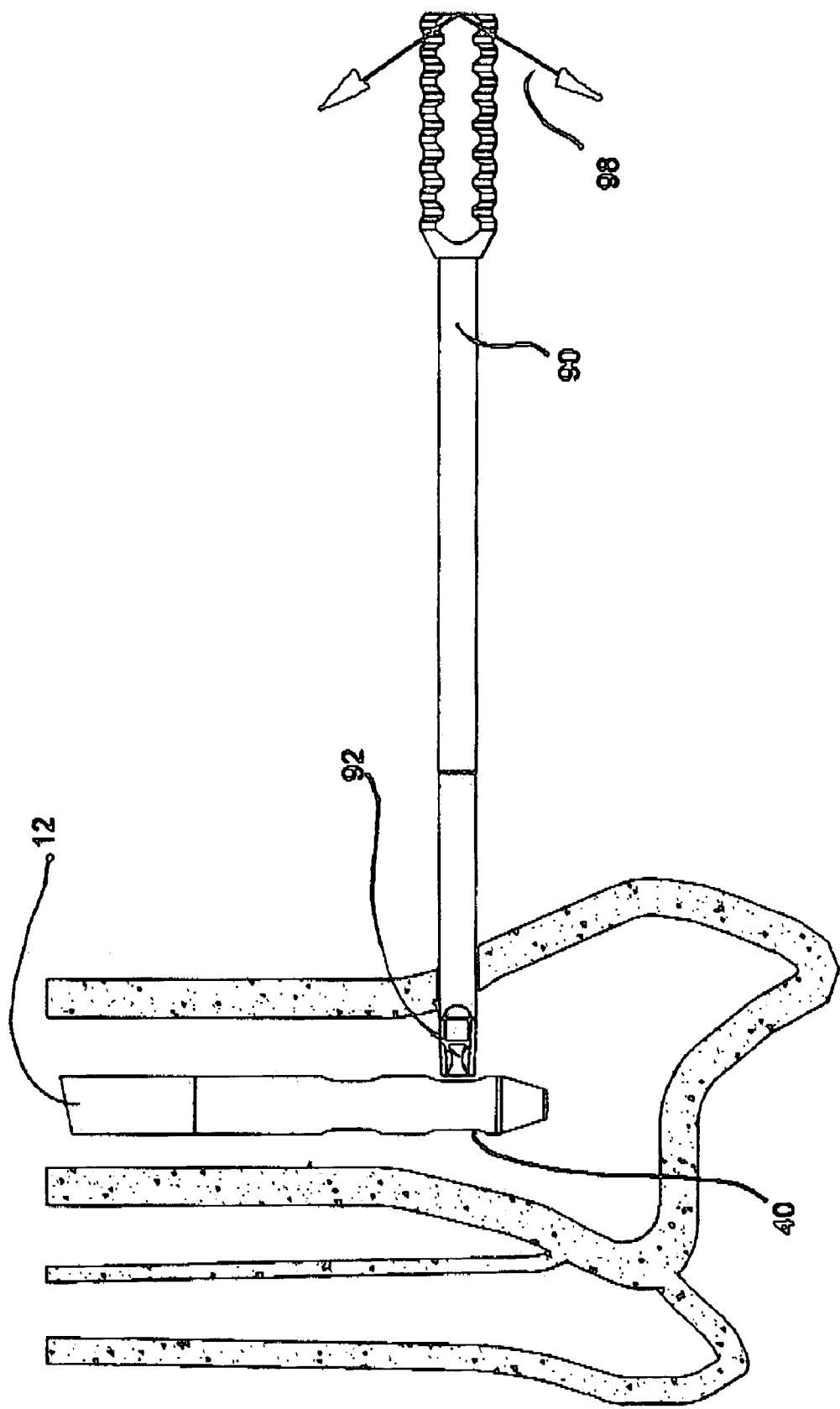
FIG. 9 illustrates the use of the slot finder after the jig has been removed.

If the slot finder 90 isn't aligned perfectly with aperture 40 in the nail (FIG. 9), the jig 17 is removed from the T-handle. The surgeon then has more freedom to search for the aperture 40 by rotating the slot finder (illustrated at 98 in FIG. 9) within the confines of the aperture 81 in the near side cortex 72.

Figure 10:
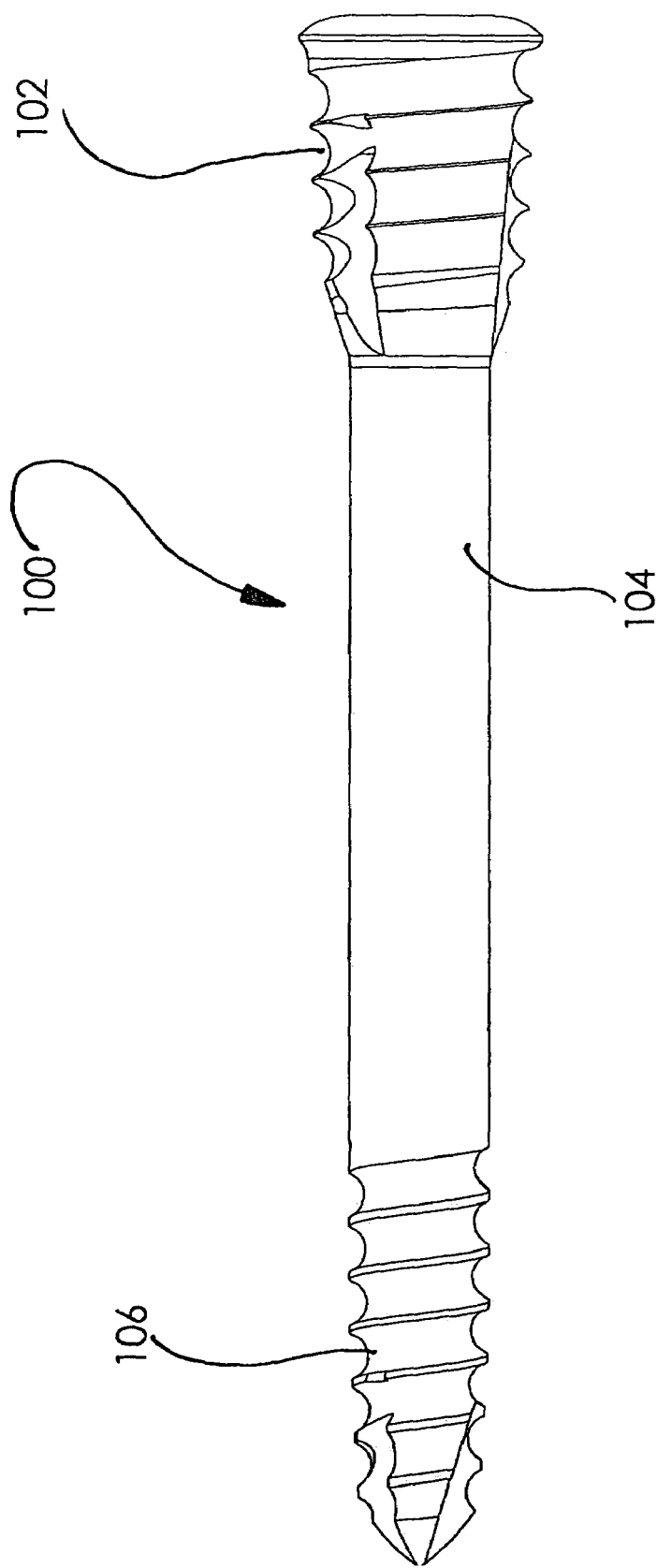
FIG. 10 illustrates the screw used to interlock the IM nail through the bone.
Figure 11:
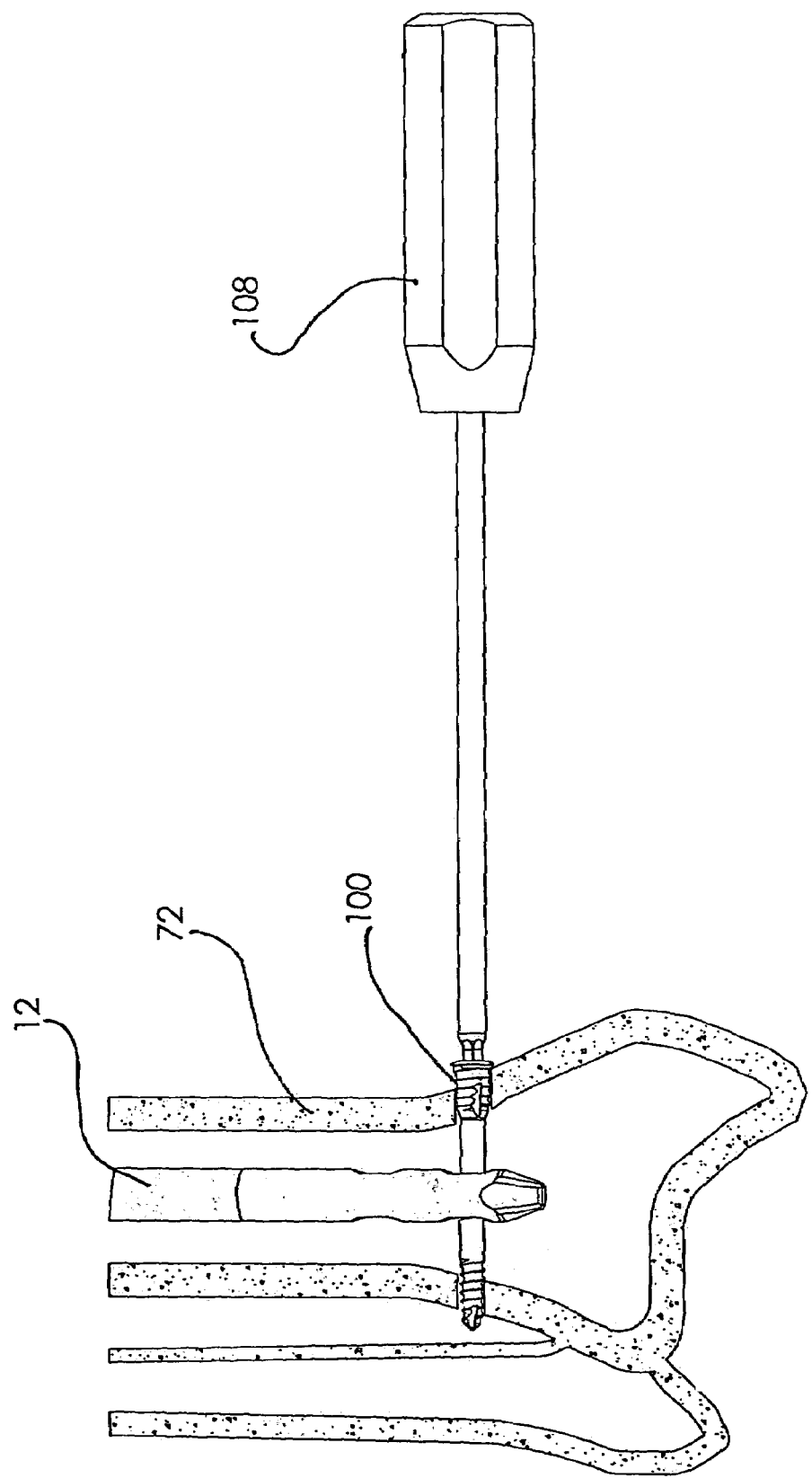
FIG. 11 illustrates the insertion of the screw through the bone apertures and slot in the nail.

After the holes have been drilled through both the near and far side bone cortex, screws may be inserted to maintain the IM nail in position. As illustrated in FIG. 10, the screw 100 used herein is preferably provided with a first threaded portion 102 having a first larger diameter, a shank portion 104, and a second threaded portion 106 having a second smaller diameter. The diameters of the, threaded portions 102, 106 are chosen such that the first larger diameter threaded portion 102 securely engages the first larger diameter aperture 81 in the near side bone cortex, and the second smaller diameter threaded portion 106 securely engages the second smaller diameter aperture 96 in the far side bone cortex. As illustrated in FIG. 11, when the apertures (81 and 96) in the bone cortex and IM nail (40) are aligned, the screw 100 may be screwed (as with a manual or powered screwdriver 108).

Figure 12:
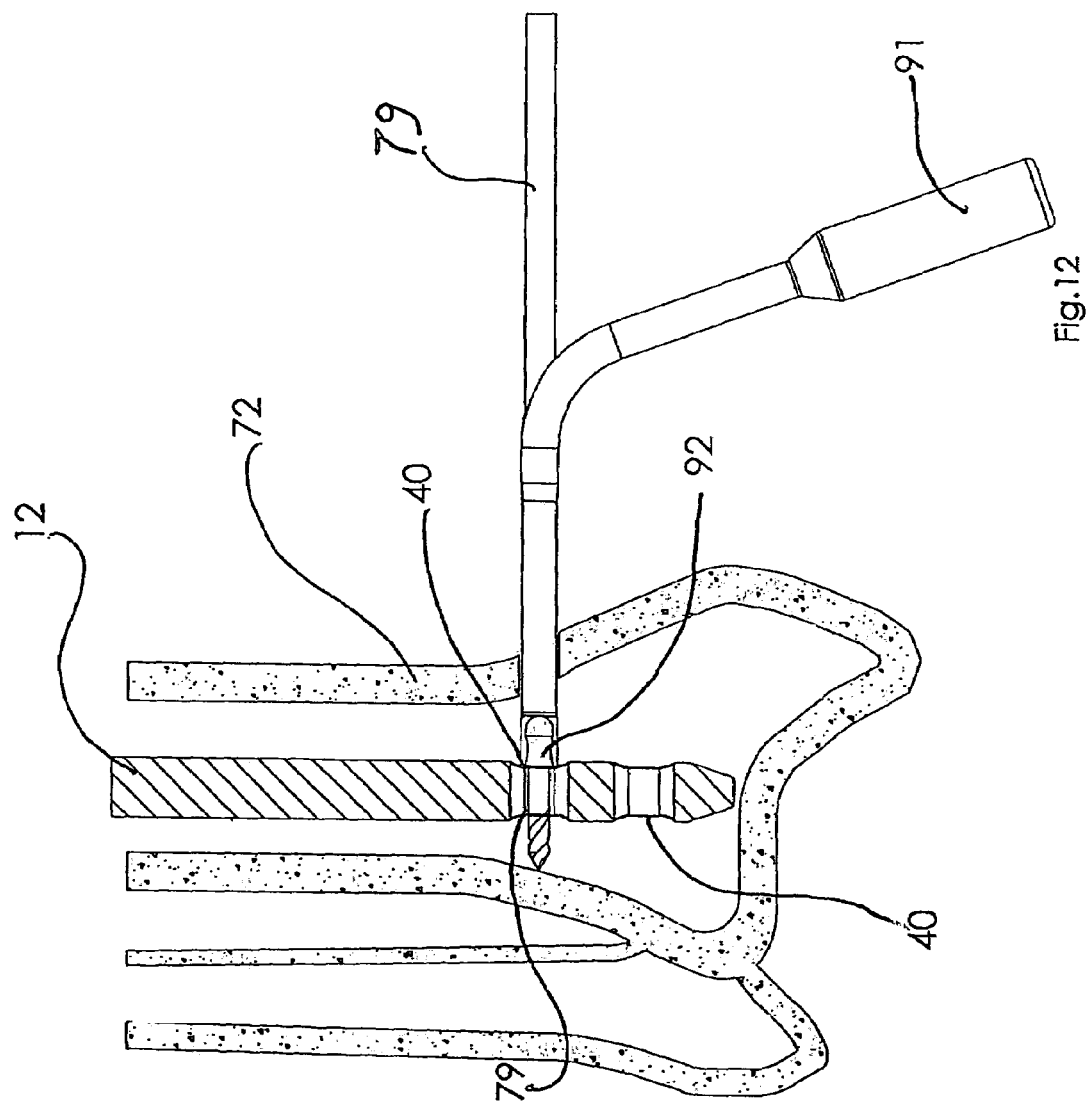
FIG. 12 illustrates an alternative cannulated slot finder.

An alternative slot finder is illustrated in FIG. 12. In this embodiment, the slot finder 91 has been inserted and the end 92 of the slot finder secured within the aperture 40. In order to assist the drilling of far-side apertures 96 and insertion of screws 100, the slot finder 91 is hollow and permits the insertion of the smaller drill bit 79 while he slot finder is engaged with the aperture 40.

The proximal target arm 18 chosen for a particular application is provided with proximal apertures 26 having a predetermined distance 82 from the axis 84 of the cap screw 20 and T-handle equal to the distance 86 between the proximal apertures 28 in IM nail 12 and the axis 84. This relationship ensures that the surgeon is able to insert screws through the apertures 28 to restrain movement of the IM nail 12. Likewise, the particular distal target arm 22 will be chosen such that when affixed to the proximal target arm 18, the distal apertures 30 are aligned with the distal apertures 40 in IM nail.

Figure 14:
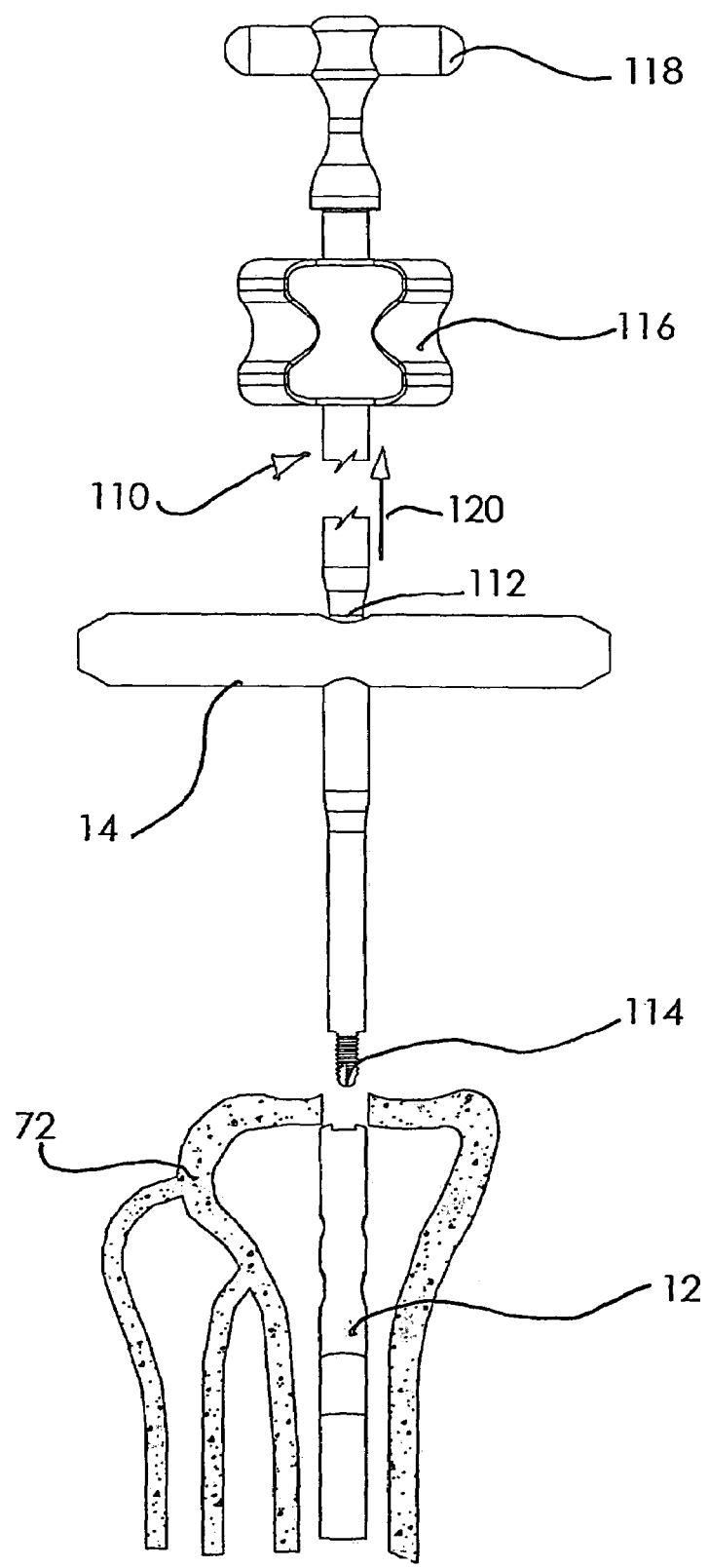
FIG. 14 illustrates the nail extraction device.

When screws 100 have been inserted into each of apertures 28, 40 of IM nail 12 (FIG. 13) the locking bolt 16 is disengaged and the T-handle 14 is withdrawn, leaving the IM nail 12 secured to the bone 72 by screws 100. After a period of time sufficient to enable the fractured bone to mend, the IM nail may be withdrawn. At that point, the screws are removed. The surgeon may then utilize a specialized nail removal device 110, as illustrated in FIG. 14. A shaft 112 is provided with a threaded portion 114 that mates either with the proximal threads of the IM nail 12 (and into which the T-handle was secured). A weight 116 is slidably engaged on the shaft 112. At the end of the shaft 112 a cap member 118 prevents the weight 116 from further longitudinal movement. To remove the IM nail, the weight is forcefully moved from the threaded end of the shaft 112 to the capped end of the shaft (in the direction of arrow 120) and upon impacting the cap 118, the IM nail is forced to move outwardly out of the bone 72.

Figure 15:
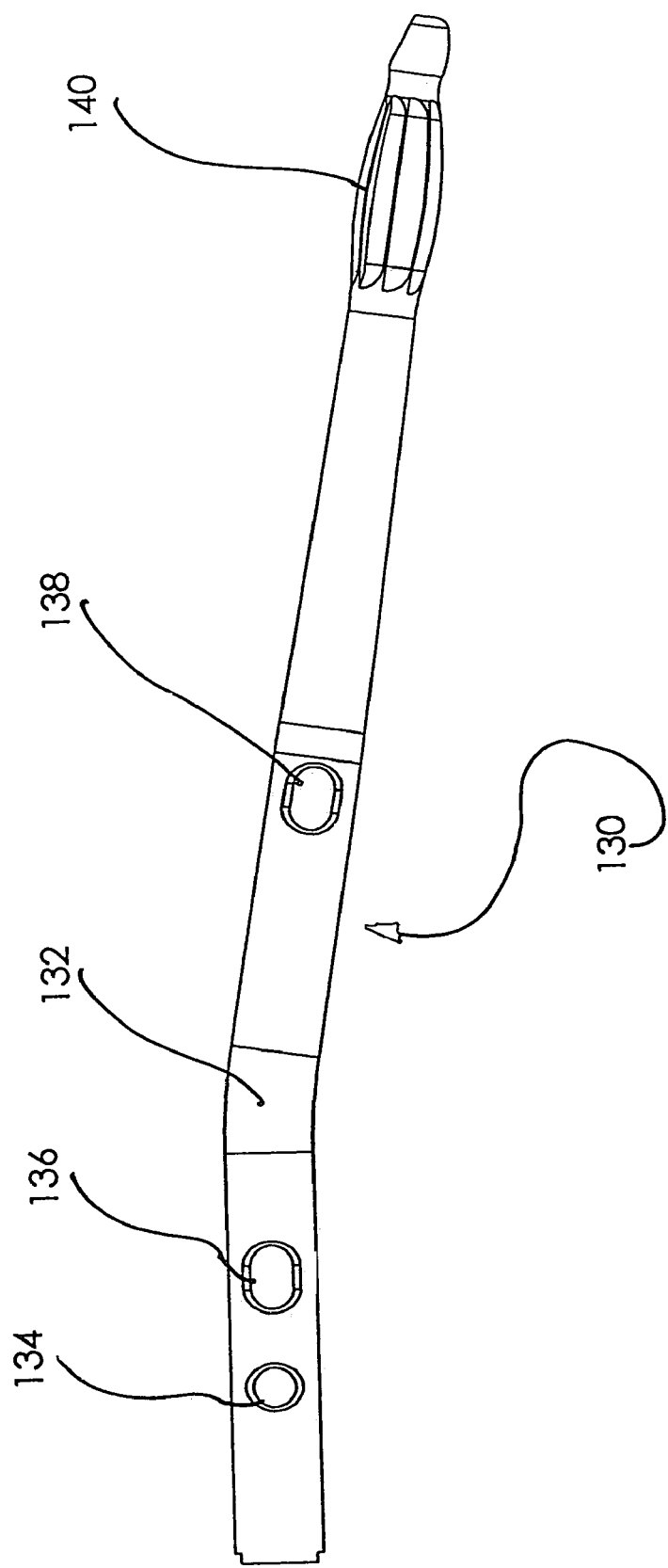
FIG. 15 illustrates the fin nail with flutes that fixate one end of the nail within the bone.

A final embodiment of an IM nail 130 is illustrated in FIG. 15 illustrating the curvature (at 132) required in many IM nails. In this embodiment, proximal apertures are illustrated at 134 and 136; the aperture 134 is a circular aperture while aperture 136 is not circular. The aperture 136 is preferably used with a slot finder having a tip with a correspondingly-shaped geometry. The distal aperture 138 is likewise not circular in geometry,. The nail 130 is provided with a fluted distal end. The nail 130 is provided with a plurality of longitudinally oriented fins 140 having a cross-sectional diameter greater than the diameter of the nail 130. The fins 140 prevent rotational movement of the nail, thereby assuring that apertures 134, 136, 138 maintain their appropriate orientation with the apertures in the jig to better insertion of the screws.

The invention described herein may be utilized either in the treatment of human patients (as for example in areas of the world where sophisticated medical practitioners and apparatus are not available) or in the treatment of animals (such as horses, cattle and other large animals) wherein sophisticated equipment is not readily available. There are other applications readily apparent for this invention, such as battlefield surgery, treatment of animals in zoos, and the like.

The device of the present invention is Illustrated in its preferred embodiments. It should be appreciated that the preferred embodiment illustrated in the drawings is but one possible mechanism to affect the principle of the present invention. In its broadest embodiment, the present invention may be comprised of any apparatus capable of ensuring alignment between an aperture drilled into the bone cortex and apertures provided in both the proximal and distal ends of an IM nail. Many different embodiments may be conceived by those having skill in this art area—the invention as described herein is merely exemplary of such embodiments.

Various modifications, variations and other embodiments of the invention may be conceived from this disclosure, and such modifications are to be considered within the context of this invention. Accordingly, the scope of the present invention should be considered limited solely by the scope of the claims appended hereto.

I claim:

1. An apparatus for locating and stabilizing an orthopedic intramedullary nail having a longitudinal axis and inserted longitudinally within the medullary cavity of a fractured long bone in an animal extremity, said apparatus comprising:
    a. an intramedullary nail having a longitudinal axis, and a plurality of target apertures therein disposed about said longitudinal axis, a portion of said apertures above a fracture in said bone and a portion of said apertures below a fracture in said bone, each of said apertures having a predetermined cross-sectional geometry;
    b. a removable handle for inserting and removing the nail;
    c. an adjustable jig removably secured to said handle comprising a proximal target arm having a plurality of apertures therein adapted to align with a plurality of apertures in a distal arm, said proximal target arm and said distal target arm adjustable relative to one another along said longitudinal axis;
    d. apparatus to drill apertures through the near cortex and the far cortex of said bone on both sides of a target aperture in said nail such that said apertures in the cortex of said bone are aligned with target apertures in said nail and apertures in said jig; and
    e. a slot finder inserted through said aperture in the near cortex of said bone and adapted to engage said target aperture, said slot finder having a cross-sectional geometry substantially identical to the cross-sectional geometry of said target apertures in said nail, such that the slot finder securely engages the target aperture in said nail, in a manner that limits the rotational movement of the slot finder when engaged with said target aperture.

2. The apparatus of claim 1, wherein said jig comprises a cannula adapted to be secured to said bone.

3. The apparatus of claim 2, wherein said jig comprises a drill guide adapted to be disposed within said cannula.

4. The apparatus of claim 3, wherein said jig comprises a drill and a first larger drill bit adapted to be disposed through said drill guide such that said larger drill bit drills a first larger aperture in the near cortex of said bone.

5. The apparatus of claim 4, wherein said slot finder comprises a leading end having a cross-sectional geometry substantially identical to the cross-sectional geometry of said target apertures.

6. The apparatus of claim 5, wherein when said leading end of said slot finder is inserted within said target aperture, the rotational movement of said slot finder is less than approximately 20° degrees.

7. The apparatus of claim 4, wherein said slot finder further comprises a bearing surface adapted to engage the exterior surface of said nail.

8. The apparatus of claim 7, wherein said jig comprises a drill guide and a second smaller drill bit adapted to be disposed through said first larger aperture in said cortex and a target aperture in said nail, and to drill a second smaller aperture in said far cortex.

9. The apparatus of claim 8, wherein a screw is inserted through said first larger aperture in said cortex, through the target aperture, and through said second smaller aperture in said cortex.

10. The apparatus of claim 9, wherein said screw is provided with a first larger threaded portion for securement in said first larger aperture in said near cortex, and a second smaller threaded portion for securement in said second smaller aperture in said far cortex.

11. The apparatus of claim 1, wherein said apparatus further comprises a device to remove said nail from said bone, comprising:
    a. an elongate shaft;
    b. a threaded portion of said shaft adapted to engage a mating threaded portion of said nail;
    c. a cap at an end of said shaft proximal from said threaded portion; and
    d. a weight slidably engaged along said shaft.

12. The apparatus of claim 11, wherein said intramedullary nail further comprises a plurality of longitudinally oriented fins at a distal end of said nail.

13. The apparatus of claim 1, wherein said intramedullary nail further comprises a plurality of longitudinally oriented fins at a distal end of said nail.

* * * * *